United States Patent [19]

Pfreundschuh et al.

[11] Patent Number: 5,861,308

[45] Date of Patent: Jan. 19, 1999

[54] ISOLATED NUCLEIC ACIDS ASSOCIATED WITH T CELL ACTIVATION AND USES THEREOF

[75] Inventors: Michael Pfreundschuh; Christoph Renner, both of Homburg/Saar, Germany

[73] Assignee: Ludwig Institute for Cancer Research, New York, N.Y.

[21] Appl. No.: 701,233

[22] Filed: Aug. 21, 1996

[51] Int. Cl.[6] .............................. C07H 21/04; C12N 1/20; C12N 15/63; C12N 15/85
[52] U.S. Cl. .................. 435/320.1; 435/325; 435/252.1; 536/23.5
[58] Field of Search ...................... 536/23.5; 435/320.1, 435/325, 252.1

[56] References Cited

PUBLICATIONS

Bernard et al. Nucleic Acid Res. 24:1435–1442, 1996.

Su et al. Cancer Res. 55:2972–2977, 1995.

Primary Examiner—Thomas M. Cunningham
Assistant Examiner—Martha Lubet
Attorney, Agent, or Firm—Fulbright & Jaworski, LLP.

[57] ABSTRACT

A group of proteins which are associated with T cell activation are disclosed, as are the nucleic acid molecules encoding them. Various uses of these materials are also discussed.

7 Claims, 2 Drawing Sheets

ISOLATED NUCLEIC ACIDS ASSOCIATED WITH T CELL ACTIVATION AND USES THEREOF

FIELD OF THE INVENTION

This invention relates to isolated nucleic acid molecules which encode proteins associated with activated T cells. The invention also relates to the encoded proteins, as well as to the use of the nucleic acid molecules and proteins in various methodologies, such as the diagnosis of pathological conditions associated with T cell activation.

BACKGROUND AND PRIOR ART

Research in the area of T cell biology has exploded in the last 10 years, and the field continues to expand, as the various roles of T cells in various biological processes become understood, or better understood.

It has now become accepted that T cells play a key role in tumor immunology. Specifically, T cells recognize various complexes of MHC Class I molecules and peptides on the surfaces of cells, and lyse these "targets". The processes by which this occurs are complex, and are discussed in many well known publications.

Decreased activity of T cells is seen in tumor patients, and it has been suggested that depression of T cell activity leads to circumvention of immunological control of tumors. Several immunotherapeutic approaches have been developed, with the common aim of restoring T cell activity in the patient. See, e.g., Pardoll, Immunol. Today 14: 310–316 (1993), Beun et al., Immunol. Today 15: 11–15 (1994), both of which are incorporated by reference, for a general overview of the field.

One of the more successful strategies which has been developed is the use of bispecific monoclonal antibodies ("Bi-MAbs" hereafter), which target and activate a broad range of resting T cells against antigen positive tumor cells, thereby inducing tumor cell destruction. See Renner & Pfreundschuh, Immunol. Rev. 145: 179–191 (1995), incorporated by reference. In a particular application of this technique, Hodgkin's lymphoma was used as a model. Combining two Bi-MAbs, the first of which consisted of one arm which recognizes Hodgkin's associated CD30 antigen, the second of which recognizes either the CD3 trigger or the CD28 trigger molecule, led to efficient tumor cell lysis, both in vitro and in vivo. See Renner et al., Science 264: 833–835 (1994), incorporated by reference. As reported by Renner et al., Blood 87: 2930–2937 (1996), SCID mice bearing Hodgkin's lymphoma responded favorably to this approach.

Additional studies on the mechanisms involved in Bi-MAb mediated T cell activation and tumor cell lysis, revealed that multiple activation markers, cytokines, and cytokine proteins, are upregulated rapidly after combined CD3 and CD28 antigen crosslinking. See Renner et al., Eur. J. Immunol. 25: 2027–2032 (1995). The effectiveness of this approach is based on the fact that Bi-MAb mediated T cell stimulation mimics the physiological pathways of T cell activation, which depend on two signals. As a rule, one signal is delivered by activation of the T cell receptor, via a peptide presented in an MHC restricted fashion, and the second, distinct signal is provided via the interaction of the CD28 antigen on T cells, and a member of the B-7 family on the corresponding "APC", or antigen presenting cell. See Linsley et al., J. Exp. Med. 173: 721–730 (1991); Linsley et al., Ann. Rev. Immunol. 11: 191–212 (1993).

Expression of genes in cells is frequently related to the effect of various molecules on cells. Study of the changes in expression of various genes requires that one have various analytical models available for deployment. One such method is differential display, or differential mRNA display. This method is taught by Liang et al., Science 257: 967–971 (1992); Liang et al., Curr. Opin. Immunol. 7: 274–280 (1995), both of which are incorporated by reference, as well as in U.S. Pat. No. 5,762,311 to Pardee and Liang, also incorporated by reference. Briefly, performance of this methodology requires the isolation of total RNA from two cell populations which are to be compared. Following isolation, first strand copies of both RNAs are made by reverse transcription, using oligo-dT primers having specific dinucleotides at their end. This is followed by a polymerase chain reaction, wherein this 3'-primer and an arbitrary 5'-primer are used for the generation of cDNA fragments. The use of the short, arbitrary primers frees the investigator from the need to depend on known DNA sequences, and makes it much easier to search for unknown genes.

Investigations have been carried out wherein differential display methodologies have been used to isolate genes which are differentially expressed in malignancies (e.g. brain tumors), heart disease and diabetes. See Zhang et al, Mol. Carcinog. 8: 123–126 (1993), Utans et al., Proc. Natl. Acad. Sci. U.S.A. 91: 6463–6467 (1994); Joseph et al., Biochem. Biophys. Res. Comm. 20: 1227–1234 (1994). This approach has also been used for breast cancer studies, and several cDNA fragments were characterized which are upregulated in tumor cells, as compared to normal tissues. The role of these genes in tumorigenesis remains to be elucidated. See Liang et al., Cancer Res. 52: 6966–6968 (1992).

The present application involves the application of the differential display technique to T cell activation, and the identification of molecules involved in this process. Specifically, the application is directed to the identification of those molecules which are differentially expressed following combined stimulation by CD3 and CD28 trigger molecules. This will be clear from the disclosure which follows.

EXAMPLE 1

Figure 1:
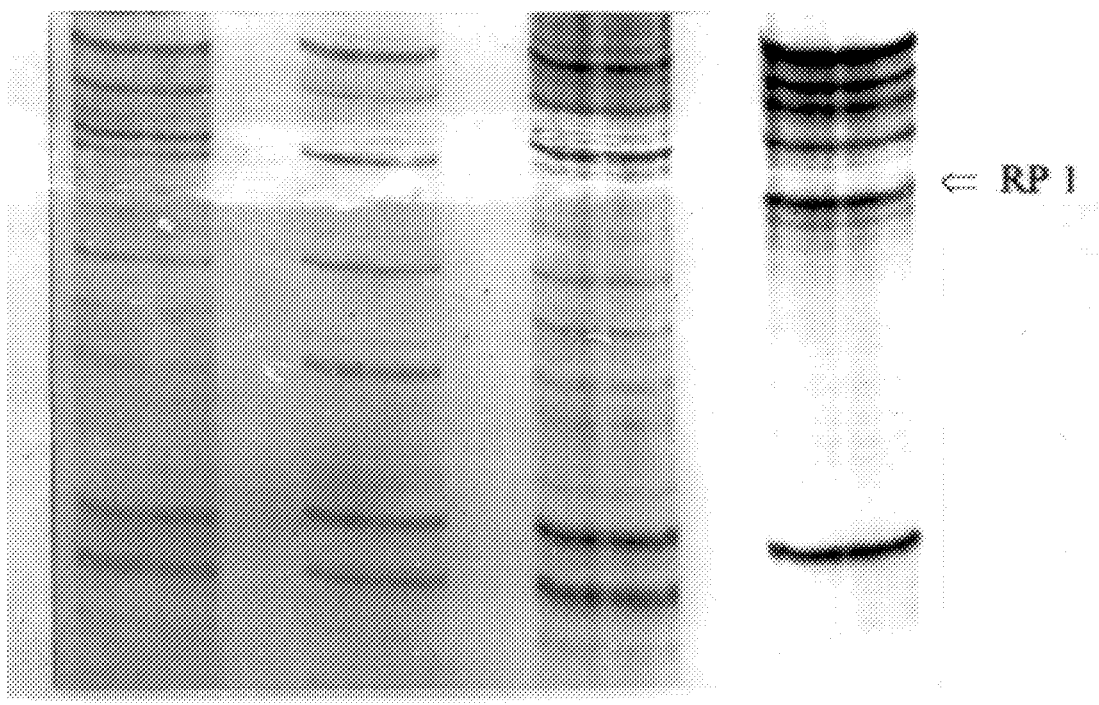
FIG. 1 depicts differential mRNA display, which was obtained by stimulating T cells with various monoclonal antibodies. The band corresponding to RP1 is indicated as such.

The experiments described herein were designed to find expression of genes involved specifically in T cell activation.

Resting T cells and activated T cells were used. The latter had been activated by contact with Bi-MAbs, as described by, e.g., Renner et al., Immunol. Rev. 145: 179–191 (1995), incorporated by reference. Bi-MAbs, as described by Renner et al, are known to target and to activate a broad range of resting T cells, such that these are active against antigen positive tumor cells, and thus induce tumor cell destruction. The Bi-MAbs used included one arm which recognizes a Hodgkin's associated antigen, "CD30", and another arm which recognized either the CD3 trigger molecule or the CD28 trigger molecule. See Renner et al., Science 264: 833–835 (1994), incorporated by reference. Also see Renner et al., Blood 87: 2930–2937 (1996), incorporated by reference. Both Renner publications describe how to make these Bi-MAbs.

T cell samples were secured by isolating peripheral blood mononuclear cells, using established techniques, followed by negative enrichment of T cells, using the MACS technique of Renner et al., Eur. J. Immunol. 25: 2027–2032 (1995), incorporated by reference. Following application of the technique, the remaining lymphocytes were >95% CD3+. The contaminating cell fractions were always below 0.5%, and no proliferation was observed, following stimulation with PMA (10 ng/ml), or PHA (100 ng/ml), over a 2–5 day period.

Samples from two healthy donors were treated in this way. Once the T cells were purified, portions of each sample were activated, via combining the T cells with 200 ng/ml of each of the Bi-MAbs anti-CD3/CD30 and anti-CD28/CD30, in the presence of the CD30 fusion protein CD30-FP, as described by Renner et al., Eur. J. Immunol. 25: 2027–2032 (1995), incorporated by reference. Renner's protocol for activation was followed, for up to 48 hours. Controls included culturing of samples with one Bi-MAb, or with no antibodies, using the same conditions as were used with both Bi-MAbs.

Following activation, mRNA was isolated from the T cells, using standard methods, and then used in an mRNA differential display system, following Liang et al., Nucl. Acid Res. 21: 3269–3275 (1993), incorporated by reference. In particular, 2 ug samples of total cellular RNA were combined with 1 unit of DNase I, in a 10 ul volume for 30 minutes at 37° C., to abolish chromosomal DNA contamination. Reverse transcription of 4 ul of DNA free RNA was performed using two oligo d(T) anchor primers [d(T)$_{11}$GC and d(T)$_{11}$CG] for 60 minutes. The remaining RNA was digested by adding 1 unit RNAse, to each vial. PCR was then carried out, in accordance with Bauer et al., Nucl. Acids. Res. 21: 4272–4280 (1993), incorporated by reference, using one anchor primer and a combination of two random decamer primers. The radioactive nucleotide $^{33}$PDATP was used as marker. Parameters included a cycle of: five minutes at 95° C., followed by one minute at 94° C., one minute at 40° C., and one minute at 72° C. Forty cycles were carried out, followed by one of 8 minutes at 72° C. The resulting, amplified cDNA was separated on a 6% polyacrylamide DNA sequencing gel. Any bands of interest were cut from the gel, the cDNA eluted, and PCR repeated. The amplified and purified cDNA was cloned into plasmid PCRII using commercially available products, followed by sequencing using known methods.

A total of 20 PCRs were carried out using different primers, resulting in approximately 2000 cDNA fragments. Analysis showed that fifteen of these were specific to stimulation by the two Bi-MAbs. One cDNA, referred to as "RP1" hereafter, was used in further experiments.

EXAMPLE 2

In order to prove the hypothesis that differential expression had occurred, Northern Blot analysis was carried out.

Using the cells and methods discussed in example 1, supra, total RNA was isolated, and a 20 ug sample was fractionated on a 10% formaldehyde agarose gel, followed by transfer cross-linking to nitrocellulose. Blots were hybridized with a $^{32}$PdCTP labelled probe, in a formamide buffer system (50% formamide, 5xSSC, 5xDenhardts, 1% SDS, 200 ug/ml heat denatured salmon sperm), for 12–16 hours at 42° C., followed by two washes at 42° C. for 15 minutes for 12–16 hours, followed by 24–48 hours of X-ray film exposure. The probe used was the RP1 mRNA discussed in example 1, supra. As controls, a 700 base pair cDNA fragment which covered a part of the coding region of the TCR associated zeta-chain, or a GADPH cDNA.

FIG. 1 presents these results, and shows a single, 2.6 kilobase transcript.

EXAMPLE 3

The cDNA fragment found in example 1 was 350 base pairs long, while Northern Blotting showed a 2.6 kb transcript. In view of the difference, RACE PCR, in accordance with Frohmann et al., Proc. Natl. Acad. Sci. U.S.A. 85: 8998–9002 (1988), incorporated by reference, was carried out. In particular, poly(A) mRNA was purified from 100 ug of total RNA extracted from activated T cells, and a commercial RACE kit was used, to generate a full length cDNA. The resulting cDNA was cloned into plasmid PCRII, using standard methods.

Standard sequencing methodologies were carried out, and SEQ ID NO: 1 presents the sequence. The sequence is 2.6 kb long.

An open reading frame is found over nucleotides 114–1121, leading to a putative, 327 amino acid protein, with a calculated molecular weight of about 37 kilodaltons.

EXAMPLE 4

Additional RACE-PCR experiments were then carried out, which paralleled those described supra. Two additional nucleotide sequences with high homology to SEQ ID NO: 1 were found. The are referred to as RP2 and RP3, respectively. A portion of RP2 nucleotide sequence is set out at SEQ ID NO: 2.

The sequence of RP1, at both the nucleotide and deduced amino acid level, shows significant homology with the known EB1 gene family. RP1 showed highest homology with a sequence referred to as EB2, and reported by Su et al., Canc. Res. 55: 2972–2977 (1995).

EXAMPLE 5

The Northern blot analysis discussed supra showed that RP1 expression was induced only in activated T cells. Given the homology with EB2, probing to confirm this was carried out using probes derived from the 3'-end of the sequence.

The upregulation of RP1 message which occurred when stimulated by the two Bi-MAbs was observed to occur when the CD3 costimulatory second signal was mediated by a cytokine, such as IL-2, rather than CD28, although these data are not provided. Signalling by either CD3 specific antibody, or by cytokine alone, did not influence the level of expression.

When the kinetics of RP1 mRNA expression were studied, it was observed that mRNA expression was rapid, and peaked about four hours after activation.

When purified T cell subpopulation were studied, the highest level of transcript was found in CD8+ lymphocytes.

EXAMPLE 6

A series of experiments were carried out to study RP1 expression in various tumor derived cell lines. In these experiments, 15 ug of total mRNA was extracted from different tumor cell lines or T cells, using the methodologies discussed supra. In addition, 2×10$^6$ cells of each cell line were tested in cell cycle analysis, in accordance with Renner et al., Eur. J. Immunol. 25: 2027–2032 (1995), incorporated by reference. Resting and activated T cells were tested (lanes 1 and 2 of FIG. 2, respectively), as were different Hodgkin derived cell lines L428 (lane 3), and L540 (lane 4), as well as HDLM (lane 5), KMHZ (lane 6), Jurkat (lane 7), resting PBLs (lane 8), Daudi (lane 9), K562 (lane 10), U937 (lane 11), KARPAS (lane 12), and HPB-ALL (lane 13). The probe used was RP1 cDNA (SEQ ID NO: 1), with the GAPDH fragment being uses as a control.

Figure 2:
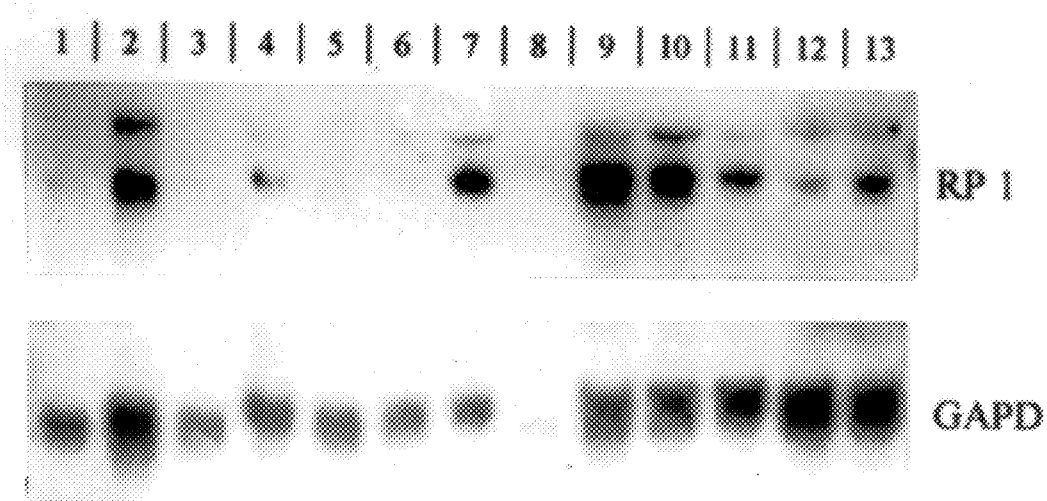
FIG. 2 presents the results of experiments designed to determine RP1 expression in various tumor derived cell lines.

The data seen in FIG. 2 show that expression of RP1 in different tumor cell lines varied considerably. There was a correlation between RP1 expression and proliferative activity of respective cell lines. Rapidly dividing cells with a high proportion of cells in S/M/G2 cell cycle phases had the highest level of RP1 expression. Evidence of this can be seen in the Hodgkin's derived cell lines L428 and HDLM2, which have only 22% cells in the S/M/G2 phase, and no or only low levels of expression. In contrast, the rapidly dividing K562 and Daudi cells, which have 73% their cells in the S/M/G2 phase showed high levels of expression of RP1.

The foregoing examples describe several isolated nucleic acid molecules, referred to herein as nucleic acid molecules which encode RP1, RP2, and RP3 (SEQ ID NOS: 1 and 2, respectively). These isolated nucleic acid molecules are associated with activated T cells. Thus, one aspect of the invention involves isolated nucleic acid molecules such as those set forth in SEQ ID NOS: 1 and 2, which are characteristic of activated T cells. Also a part of the invention are those isolated nucleic acid molecules which hybridize to either or both of SEQ ID NOS: 1 or 2, under stringent conditions. "Stringent conditions" as used herein, refers to conditions at least as stringent as a wash with 1.0×SSC for 15–30 minutes at 42° C. One could wash at higher temperatures, and /or lower SSC concentrations, with appropriate changes in other parameters.

Also a part of the invention are expression vectors which include the above mentioned sequences operably linked to a promoter, and cells, such as eukaryotic and prokaryotic cells, transfected or transformed by the above mentioned nucleic acid molecules or vectors.

The nucleic acid molecules of the invention may be used diagnostically as they will hybridize to transcribed mRNA, or more stable cDNA, and facilitate the identification of activated T cells, or indicate that a T cell population has been inactivated. Thus, a screening methodology is provided wherein one may determine whether or not a T cell related disorder, such as those listed supra, exists.

Also a feature of this invention are the isolated proteins encoded by the aforementioned nucleic acid molecules. These proteins are clearly associated with T cell activation, and thus one expects them to be useful as T cell activators. Further, antagonists of these molecules in contrast, would be expected to be T cell inhibitors. Such antagonists are useful in conditions characterized by T cell shooting or overshooting.

The proteins and/or peptides derived therefrom are large enough to be immunogenic, and antibodies can be produced against these protein and peptides, using standard techniques. These polyclonal and monoclonal antibodies are another feature of the invention, as is their use in diagnostic assays to identify the presence of the T cell activating protein, via practice of standard immunoassays.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule which comprises the nucleotide sequence of SEQ ID NO: 1 or SEQ ID NO: 2.

2. Isolated nucleic acid molecule which encodes a protein having a molecular weight of about 37 kilodaltons which is upregulated in a T cell following activation of said T cell, the complement of said isolated nucleic acid molecule hybridizing, under stringent conditions with a nucleotide sequence comprising SEQ ID NO: 1.

3. Expression vector comprising the isolated nucleic acid molecule of claim 1, operably linked to a promoter.

4. Expression vector comprising the isolated nucleic acid molecule of claim 2, operably linked to a promoter.

5. Transformed or transfected cell, comprising the expression vector of claim 3.

6. Transformed or transfected cell, comprising the expression vector of claim 4.

7. The isolated nucleic acid molecule of claim 2, wherein said T cell is activated following contact with an anti CD3/CD30 Bi-monoclonal antibody and an anti CD28/CD30 Bi-monoclonal antibody.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 2606 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
CTAGAATTCA  GCGGCCGCTG  AATTCTAGCG  AGCAGGCGGC  AGGCACGGTC                        50

CGTGCGGAGA  GGCGAGCGAG  CGGGAAGACG  CAGCCACCTT  CCTCACCAGC                       100

CAGCCCACAG  CGGTTTGTTC  CCCTTCTCGG  GAGTGCGCCA  ATG  CCT  GGG  CCG               152
                                                  Met  Pro  Gly  Pro

ACC  CAA  ACC  CTG  TCC  CCA  AAT  GGC  GAG  AAC  AAC  AAC  GAC  ATC  ATC  CAG  GAT   203
Thr  Gln  Thr  Leu  Ser  Pro  Asn  Gly  Glu  Asn  Asn  Asn  Asp  Ile  Ile  Gln  Asp
  5                   10                  15                  20

AAT  AAC  GGG  ACC  ATC  ATT  CCT  TTC  CGG  AAG  CAC  ACA  GTG  CGC  GGG  GAG  CGT   254
Asn  Asn  Gly  Thr  Ile  Ile  Pro  Phe  Arg  Lys  His  Thr  Val  Arg  Gly  Glu  Arg
              25                  30                          35

TCC  TAC  AGT  TGG  GGA  ATG  GCG  GTC  AAT  GTG  TAT  TCT  ACC  TCG  ATA  ACC  CAA   305
Ser  Tyr  Ser  Trp  Gly  Met  Ala  Val  Asn  Val  Tyr  Ser  Thr  Ser  Ile  Thr  Gln
```

-continued

|  | 40 |  |  |  | 45 |  |  |  | 50 |  |  |  | 55 |  |  |  |
|---|---|---|---|---|---|---|---|---|---|---|---|---|---|---|---|---|
| GAG | ACT | ATG | AGC | AGA | CAT | GAC | ATC | ATT | GCA | TGG | GTT | AAT | GAC | ATA | GTA | TCT | 356 |
| Glu | Thr | Met | Ser | Arg 60 | His | Asp | Ile | Ile 65 | Ala | Trp | Val | Asn | Asp 70 | Ile | Val | Ser |  |
| TTA | AAC | TAC | ACA | AAA | GTG | GAA | CAG | CTT | TGT | TCA | GGA | GCG | GCC | TAT | TGC | CAA | 407 |
| Leu | Asn | Tyr 75 | Thr | Lys | Val | Glu | Gln 80 | Leu | Cys | Ser | Gly | Ala 85 | Ala | Tyr | Cys | Gln |  |
| TTC | ATG | GAC | ATG | CTC | TTC | CCT | GGC | TGC | ATT | AGT | TTG | AAG | AAA | GTA | AAA | TTT | 458 |
| Phe 90 | Met | Asp | Met | Leu | Phe 95 | Pro | Gly | Cys | Ile | Ser 100 | Leu | Lys | Lys | Val | Lys 105 | Phe |  |
| CAA | GCA | AAG | CTG | GAA | CAT | GAA | TAT | ATT | CAC | AAT | TTT | AAA | CTT | CTG | CAA | GCA | 509 |
| Gln | Ala | Lys | Leu 110 | Glu | His | Glu | Tyr | Ile 115 | His | Asn | Phe | Lys | Leu 120 | Leu | Gln | Ala |  |
| TCA | TTT | AAG | CGA | ATG | AAC | GTT | GAT | AAG | GTA | ATT | CCA | GTG | GAG | AAG | CTA | GTG | 560 |
| Ser | Phe 125 | Lys | Arg | Met | Asn | Val 130 | Asp | Lys | Val | Ile | Pro 135 | Val | Glu | Lys | Leu | Val 140 |  |
| AAA | GGA | CGT | TTC | CAG | GAC | AAC | CTG | GAT | TTT | ATT | CAA | TGG | TTT | AAG | AAA | TTC | 611 |
| Lys | Gly | Arg | Phe | Gln 145 | Asp | Asn | Leu | Asp | Phe 150 | Ile | Gln | Trp | Phe | Lys 155 | Lys | Phe |  |
| TAT | GAT | GCT | AAC | TAC | GAT | GGG | AAG | GAG | TAT | GAT | CCT | GTA | GAG | GCA | CGA | CAA | 662 |
| Tyr | Asp | Ala | Asn 160 | Tyr | Asp | Gly | Lys | Glu 165 | Tyr | Asp | Pro | Val | Glu 170 | Ala | Arg | Gln |  |
| GGG | CAA | GAT | GCA | ATT | CCT | CCT | CCT | GAC | CCT | GGT | GAA | CAG | ATC | TTC | AAC | CTG | 713 |
| Gly 175 | Gln | Asp | Ala | Ile | Pro 180 | Pro | Pro | Asp | Pro | Gly 185 | Glu | Gln | Ile | Phe | Asn 190 | Leu |  |
| CCA | AAA | AAG | TCT | CAC | CAT | GCA | AAC | TCC | CCC | ACA | GCA | GGT | GCA | GCT | AAA | TCA | 764 |
| Pro | Lys | Lys | Ser 195 | His | His | Ala | Asn | Ser 200 | Pro | Thr | Ala | Gly | Ala 205 | Ala | Lys | Ser |  |
| AGT | CCA | GCA | GCT | AAA | CCA | GGA | TCC | ACA | CCT | TCT | CGA | CCC | TCA | TCA | GCC | AAA | 815 |
| Ser | Pro 210 | Ala | Ala | Lys | Pro | Gly 215 | Ser | Thr | Pro | Ser | Arg 220 | Pro | Ser | Ser | Ala | Lys 225 |  |
| AGG | GCT | TCT | TCC | AGT | GGC | TCA | GCA | TCC | AAA | TCC | GAT | AAA | GAT | TTA | GAA | ACG | 866 |
| Arg | Ala | Ser | Ser | Ser 230 | Gly | Ser | Ala | Ser | Lys 235 | Ser | Asp | Lys | Asp | Leu 240 | Glu | Thr |  |
| CAG | GTC | ATA | CAG | CTT | AAT | GAA | CAG | GTA | CAT | TCA | TTA | AAA | CTT | GCC | CTT | GAA | 917 |
| Gln | Val | Ile | Gln 245 | Leu | Asn | Glu | Gln | Val 250 | His | Ser | Leu | Lys | Leu 255 | Ala | Leu | Glu |  |
| GGC | GTG | GAA | AAG | GAA | AGG | GAT | TTC | TAC | TTT | GGG | AAG | TTG | AGA | GAG | ATC | GAG | 968 |
| Gly | Val | Glu | Lys | Glu 260 | Arg | Asp | Phe | Tyr | Phe 265 | Gly | Lys | Leu | Arg | Glu 270 | Ile | Glu 275 |  |
| CTA | CTC | TGC | CAA | GAA | CAC | GGG | CAG | GAA | AAT | GAT | GAC | CTC | GTG | CAG | AGA | CTA | 1019 |
| Leu | Leu | Cys | Gln | Glu 280 | His | Gly | Gln | Glu | Asn 285 | Asp | Asp | Leu | Val | Gln 290 | Arg | Leu |  |
| ATG | GAC | ATC | CTG | TAT | GCT | TCA | GAA | GAA | CAC | GAG | GGC | CAC | ACA | GAA | GAG | CCG | 1070 |
| Met | Asp | Ile | Leu | Tyr 295 | Ala | Ser | Glu | Glu | His 300 | Glu | Gly | His | Thr | Glu 305 | Glu | Pro 310 |  |
| GAA | GCA | GAG | GAG | CAA | GCC | CAC | GAA | CAG | CAG | CCC | CCG | CAG | CAG | GAA | GAG | TAC | 1121 |
| Glu | Ala | Glu | Glu | Gln 315 | Ala | His | Glu | Gln | Gln 320 | Pro | Pro | Gln | Gln | Glu 325 | Glu | Tyr |  |

```
TGACCCACCC CGGCTGCTCT TGACACTTCC ATTGTGTGTG GGAACGTTTC TTCTGGAGAA   1181
TTGGAACATG TGTGGCCCCA AGCTCAACAG AAACCAGTTG TTCCCAATCT GCCGTTACCA   1241
TCAACGCACT GTTGCATATG CCAGCCACTG CGCTTGGTTC CCATTTTCTT TGCTAAGGTG   1301
TATTAGCGGA CGGCCCTCTG CCACCTACC CGAGAGATCG TAGGGTCACA TTCATCCAAC   1361
TTCACCACTT GGCTGCTTGA GATTGGTTCT GCTCTTTTCT TCATTCCTTT CCAGAACAAC   1421
TCTTTCCCAC CCCAACACCA CTGCCACCAC CCCTCTTTTT ATCCTGGTGT GAAACAATGG   1481
TAATTTGATA TATGGTATTT ATATTGGCAT TTTTCAACCC AGTGTCACTA GATGTCACAC   1541
```

-continued

| | | | | | | |
|---|---|---|---|---|---|---|
| ACATTTGTGG | TGCTTTGATG | TTTGCAAGTC | TAACCTCTGA | ACATAAATTT | GGTCAAATAA | 1601 |
| TTGGAACAAA | GGGAAACAGA | TACTTGATAT | GAAAGCCATA | ATGACGGTGA | CTTGTGTCGT | 1661 |
| GGGGGAAAAC | ATAAGGTCAT | TTTCTCCCTC | TACTCACAAT | ACTAAAGGGA | AAAAATGGAT | 1721 |
| TCAAAGCTAG | GATTTCAGGG | CCCAGCAGTG | TTCCTCCATC | AGCATGTTAG | ACAACTACAC | 1781 |
| AGTATGTTGT | TAGTTTTGAA | AGACATTCAC | TCAAGGAAAA | CACCATCTCA | ACTTTGCCCG | 1841 |
| CTCACCATGT | CCCTTGCCCC | CATGTAGCCC | ATTTCCCAGG | TTATGCTCTT | TTCTTTCTCA | 1901 |
| GGGTCCTCTT | TGGTGGGCAG | CCACTCCCCG | AGATGTTGCC | ATCAGTTTTC | TGCAGTCCAA | 1961 |
| AGAGGGTATG | GTTAGGTACG | GGTCTTCCTG | CCTCATTCCT | CTTCCTCTTT | GTGTAGGTTT | 2021 |
| CAGCCACAAA | ACTGTCATTC | ACTCTAGGGG | ACCCCTACTA | AAGGGTAACT | TCAGGTGTGC | 2081 |
| AGCCCTGAGC | TCCAAGGCTC | TGCACCATGC | CACACACTTG | CTGTAAGGCT | AGAAGTGAAG | 2141 |
| ACCTTATTAA | TAGGAGCATA | ATTGCGAGGG | AGAATCATGG | TTCTGCAGTC | TGGTGTAGAC | 2201 |
| ACTGGAATAA | CAGCACAGAA | AAATCTATGA | CTCCCAATAT | CTTCTAGAAT | AAAGAATTTT | 2261 |
| CCCTCTTTAA | CACAAGGGCC | CTCCTTGTCA | TTGACCTTAG | CTAAACCATG | GCAATTCATA | 2321 |
| AATAGAGGAA | ACATTAATGA | ATTAAAAGCA | TTCCTTATTT | TTTAACTAAT | ATTTGTACAT | 2381 |
| TTTCTTAGTC | TCTTTCCAAG | TCTTTGCCTC | TTTTTTTCT | TTATTTTAT | TTTTCCTTT | 2441 |
| GACAGATGGT | ATCCCTTCCT | GGATCATTCA | TTTCACCTTG | GTTTCTAACT | TTAGGTTTAC | 2501 |
| TTTCACTTGT | TATTTGACTT | AGCAGGTGCA | ACAAAAACAA | GAAACAAATG | TGCCCACCCC | 2561 |
| ACTTTCCGCT | TAACTGAAAA | GCTTAAAATA | AATTTCCGAA | TTATG | | 2606 |

( 2 ) INFORMATION FOR SEQ ID NO: 2:

( i ) SEQUENCE CHARACTERISTICS:
        ( A ) LENGTH: 380 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

| | | | | | | |
|---|---|---|---|---|---|---|
| GGTGAGTGGG | TAAAGTTGAG | ATGGTGTTTT | CCTTGAGTGA | ATGTCTTTCA | AAACTAACAA | 60 |
| CATACTGTGT | AGTTGTCTAA | CATGCTGATG | GAGGAACACT | GCTGGGCCCT | GAAATCCTAG | 120 |
| CTTTGAATCC | ATTTTTTCCC | TTTAGTATTG | TGAGTAGAGG | GAGAAAATGA | CCTTATGTTT | 180 |
| TCCCCCACGA | CGCAAGTCAC | CGTCATTATG | GCTTTCATAT | CAAGTATCTG | TTTCCCTTTC | 240 |
| GTTCCAATTA | TTTGACCAAA | TTTATGTTCA | GAGGTTAGAC | TTGCAAACAT | CAAAGCACCA | 300 |
| NAAANGTGCC | CACCCCACTT | TCCGNTTAAC | TGAAAAGCTT | AAAATAAATT | TCTGAATTAT | 360 |
| GTATCCCGAA | AAAAAAAAA | | | | | 380 |